United States Patent
Frankle

(12) 
(10) Patent No.: US 6,860,887 B1
(45) Date of Patent: Mar. 1, 2005

(54) SUTURE MANAGEMENT METHOD AND SYSTEM

(76) Inventor: Mark A. Frankle, 4175 Fowler Ave., Tampa, FL (US) 33617-2011

( * ) Notice: Subject to any disclaimer, the term of this patent is extended or adjusted under 35 U.S.C. 154(b) by 372 days.

(21) Appl. No.: 10/011,908

(22) Filed: Nov. 5, 2001

(51) Int. Cl.$^7$ ................................ A61B 17/04
(52) U.S. Cl. .................. 606/104; 606/148; 606/232
(58) Field of Search .............. 606/72, 73, 232, 606/104, 148, 139; 128/898; 289/17

(56) References Cited

U.S. PATENT DOCUMENTS 5,411,506 A * 5/1995 Goble et al. ................ 606/104
5,702,422 A * 12/1997 Stone ........................ 606/232

* cited by examiner

Primary Examiner—Julian W. Woo
(74) Attorney, Agent, or Firm—Edward P. Dutkiewicz

(57) ABSTRACT

A method and system of suture management aids a surgeon while tying knots in sutures during surgery to preclude suture tangling. A tubular guide has an anchoring screw with a threaded lower end and an upper end removably supported by the guide. Between the upper and lower ends is an eyelet. A pair of sutures includes a first suture of a first visual characteristic and a second suture of a second visual characteristic. Each suture has two free ends and a central portion positioned through the eyelet. At least one hollow sleeve receives there through an associated suture.

7 Claims, 4 Drawing Sheets

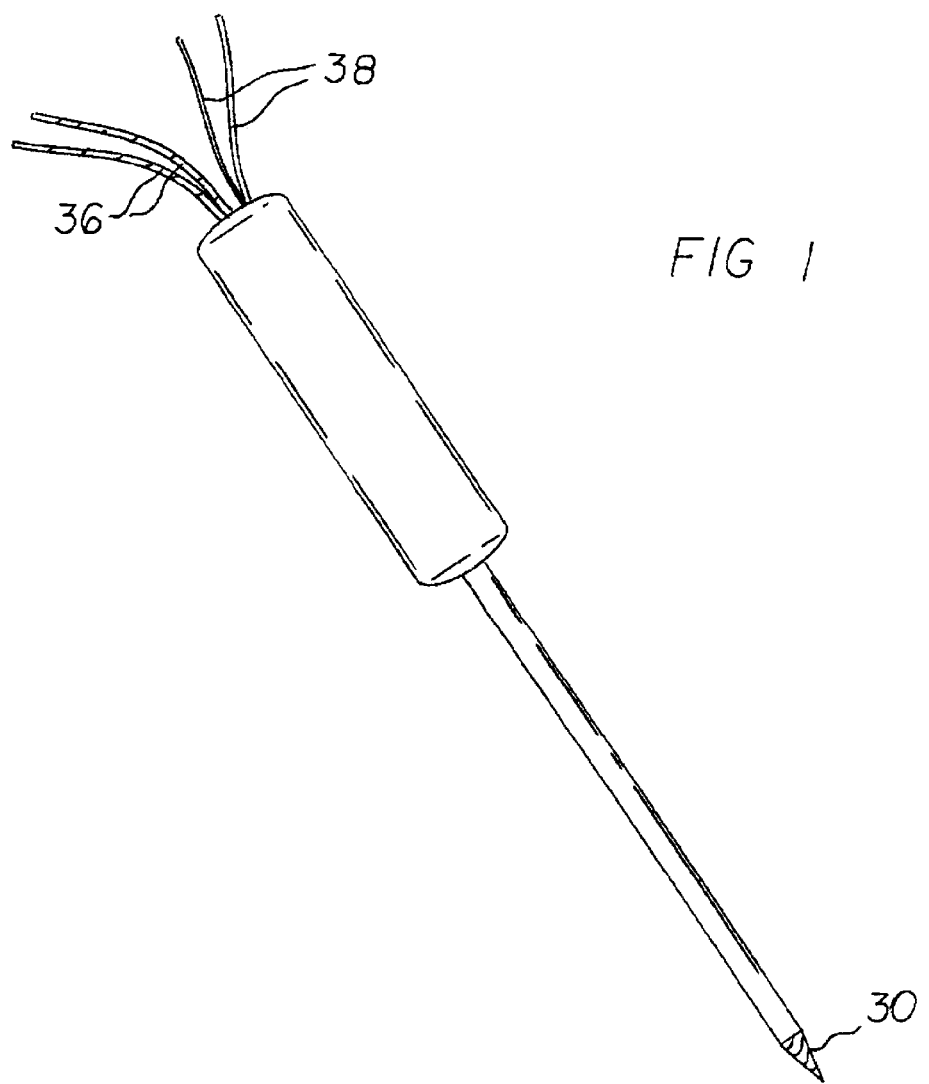

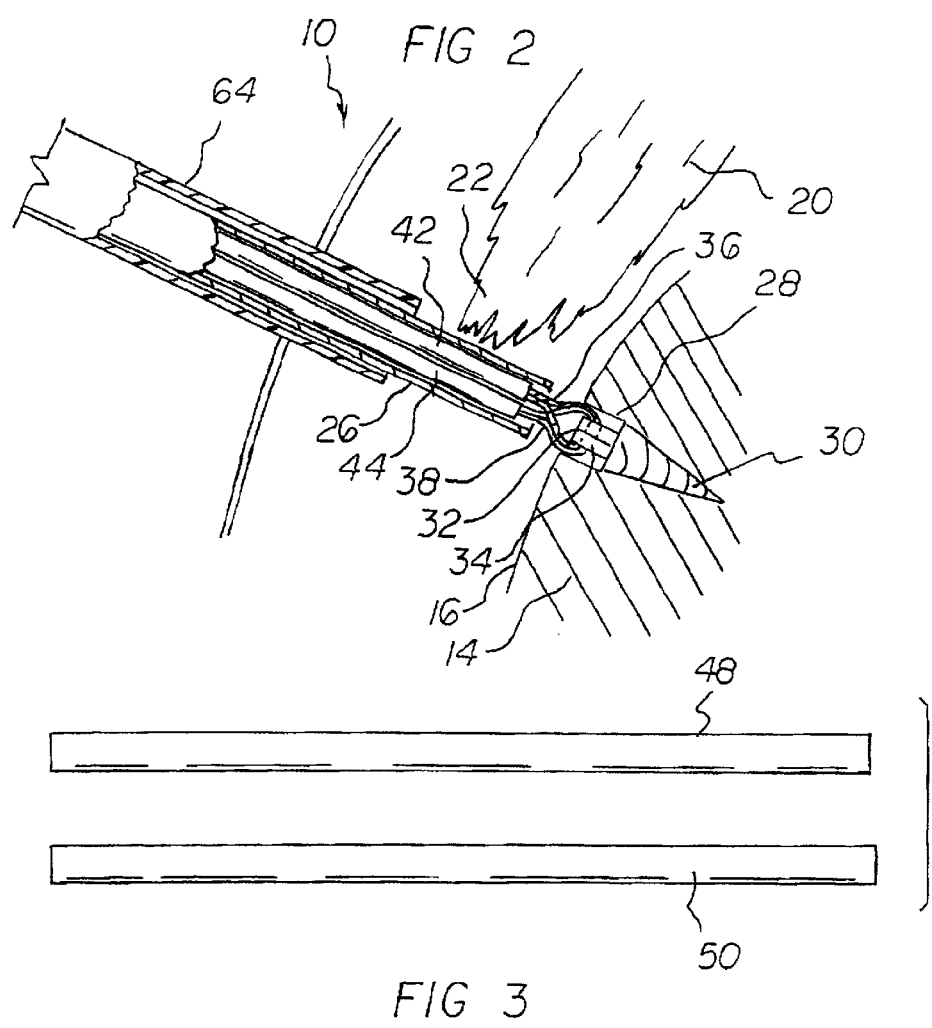

SUTURE MANAGEMENT METHOD AND SYSTEM

BACKGROUND OF THE INVENTION

1. Field of the Invention

The present invention relates to a suture management method and system and more particularly pertains to aiding a surgeon while tying knots in sutures during surgery in a manner to preclude suture tangling.

2. Description of the Prior Art

The use of old suture handling methods and apparatuses of known designs and configurations is known in the prior art. More specifically, old suture handling methods and apparatuses of known designs and configurations previously devised and utilized for the purpose of assisting a surgeon while manipulating sutures through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,476,115 to Graeff et al. discloses a ligating implement with ligature severing means. U.S. Pat. No. 4,779,616 to Johnson discloses a surgical suture-snagging method. U.S. Pat. No. 5,281,238 to Chin et al. discloses an endoscopic ligation instrument. U.S. Pat. No. 5,382,257 issued Jan. 17, 1995, to Lewis et al. discloses an implant assist apparatus. U.S. Pat. No. 5,643,320 to Lower et al. discloses a soft tissue anchor and method. U.S. Pat. No. 5,681,333 to Burkhart et al. discloses a method and apparatus for arthroscopic rotator cuff repair utilizing bone tunnels for suture attachment. U.S. Pat. No. 5,697,950 to Fucci et al. discloses a pre-loaded suture anchor. Finally, U.S. Pat. No. Re. 36,020 to Moore et al. discloses a method and apparatus for tying suture to bone.

While these devices fulfill their respective, particular objectives and requirements, the aforementioned patents do not describe a suture management method and system that allows aiding a surgeon while tying knots in sutures during surgery in a manner to preclude suture tangling.

In this respect, the suture management method and system according to the present invention substantially departs from the conventional concepts and designs of the prior art, and in doing so provides an apparatus primarily developed for the purpose of aiding a surgeon while tying knots in sutures during surgery in a manner to preclude suture tangling.

Therefore, it can be appreciated that there exists a continuing need for a new and improved suture management method and system which can be used for aiding a surgeon while tying knots in sutures during surgery in a manner to preclude suture tangling. In this regard, the present invention substantially fulfills this need.

SUMMARY OF THE INVENTION

In view of the foregoing disadvantages inherent in the known types of old suture handling methods and apparatuses of known designs and configurations now present in the prior art, the present invention provides an improved suture management method and system. As such, the general purpose of the present invention, which will be described subsequently in greater detail, is to provide a new and improved suture management method and system and method which has all the advantages of the prior art and none of the disadvantages.

To attain this, the present invention essentially comprises a suture management method and system comprised of a plurality of components and steps. Such components in their broadest context include a tubular guide, a pair of sutures, and at least one hollow sleeve. Such components are individually configured and the components and steps are correlated with respect to each other so as to attain the desired objective. A patient has a bone which would normally have a tendon attached to an exterior surface. A tendon of the patient has an end which has previously been attached to the surface of the bone. A tubular guide is provided as a component of the method and system. The guide has an anchoring screw. The screw has a threaded lower end. The screw also has an upper end removably supported by the guide. An eyelet is provided between the upper and lower ends. With such components having been provided, the invention includes the step of first providing a pair of sutures. The sutures include a first suture of a first color and a second suture of a second color. Each suture has two free ends. Each suture also has a central portion between its free ends. The central portion of both sutures is positioned through the eyelet of the screw. The next step is providing a pair of primary sleeves. The primary sleeves include a first sleeve and a second sleeve. Each primary sleeve is hollow. Each primary sleeve has an interior diameter to receive there through one suture. Each primary sleeve also has an exterior diameter less than half the interior diameter of the tubular guide. Each primary sleeve also has a length less than the distance between the free ends and the eyelet. The next step is providing a pair of supplemental sleeves. The sleeves include a first supplemental sleeve and a second supplemental sleeve. Each supplemental sleeve is hollow with an interior diameter to receive one suture there through. Each supplemental sleeve also has an exterior diameter. Each supplemental sleeve also has a length less than the distance between the free ends and the eyelet. The next step is providing a clip to apply a holding force to one supplemental sleeve with a suture therein so as to preclude relative movement between the supplemental sleeve and the suture. The next step is providing a slender plastic lasso. The lasso has a proximal end constituting a handle. The lasso has a distal end formed as a resilient loop adapted to maintain an opening when not under restraint by its positioning within a supplemental sleeve. The lasso has of a length greater than the supplemental sleeve. The next step is introducing a cannula into a patient. Next the tubular guide with the screw and the pair of sutures is introduced through the cannula into the patient. Then the screw and sutures are attached into the surface of the bone with the screw and central portions of the sutures beneath the surface of the bone. The ends of the sutures extend through the cannula to outside the patient with the suture of each color being individually constrained by a primary sleeve. The next step is retracting the tubular guide from the screw and from the cannula. The next step is removing the first primary sleeve from the first suture and from the cannula. The next step is contacting the tendon with the distal end of a supplemental sleeve to provide a temporary reduction for holding the tendon to where it is intended to be positioned until a knot is formed for a final fixation. The next step is manipulating the first suture as by forming a stitch in the tendon. The next step is positioning the first supplemental sleeve through the cannula. Then the lasso is extended through the first supplemental sleeve and the first suture is captured with the lasso. The lasso and the first suture are pulled exterior of the patient. The next step is applying the slip tot he first supplemental sleeve and first suture to create a holding force between the first supplemental sleeve and first suture and thereby rpeclude relative movement. The next step is removing the second primary sleeve from the second suture and from the cannula. The next step is manipulating the second suture as by forming a stitch in the tendon. The next step is positioning the second supplemental sleeve through the cannula. Then the lasso is extended through the second supplemental sleeve. The second suture is then captured with the lasso. Next, the lasso and the second suture are pulled exterior of the patient. The next step is removing a supplemental sleeve and manipulating a suture as may be needed. The final step is trimming the sutures and removing the trimmed ends of the sutures and the supplemental sleeves and lasso through the cannula and from the patient.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried cut in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved suture management method and system which has all of the advantages of the prior art old suture handling methods and apparatuses of known designs and configurations and none of the disadvantages.

It is another object of the present invention to provide a new and improved suture management method and system which may be easily and efficiently manufactured and marketed to the medical community.

It is further object of the present invention to provide a new and improved suture management method and system which is of durable and reliable constructions.

An even further object of the present invention is to provide a new and improved suture management method and system which is susceptible of a reasonable cost of manufacture with regard to both materials and labor, and which accordingly is then susceptible of reasonable prices of sale, thereby making such suture management method and system available to the medical community.

Even still another object of the present invention is to provide a suture management method and system for aiding a surgeon while tying knots in sutures during surgery in a manner to preclude suture tangling.

Lastly, it is an object of the present invention to provide a new and improved method and system of suture management for aiding a surgeon while tying knots in sutures during surgery to preclude suture tangling. A tubular guide has an anchoring screw with a threaded lower end and an upper end removably supported by the guide. Between the upper and lower ends is an eyelet. A pair of sutures includes a first suture of a first visual characteristic and a second suture of a second visual characteristic. Each suture has two free ends and a central portion positioned through the eyelet. At least one hollow sleeve receives there through an associated suture.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a cross sectional view of a suture management system constructed in accordance with the principles of the present invention.

FIG. 2 is a cross sectional view of a suture management system in an initial position for use.

FIG. 3 is a front elevational view of two supplemental sleeves used with the suture management system.

The same reference numerals refer to the same parts throughout the various Figures.

DESCRIPTION OF THE PREFERRED EMBODIMENT

Figure 4:
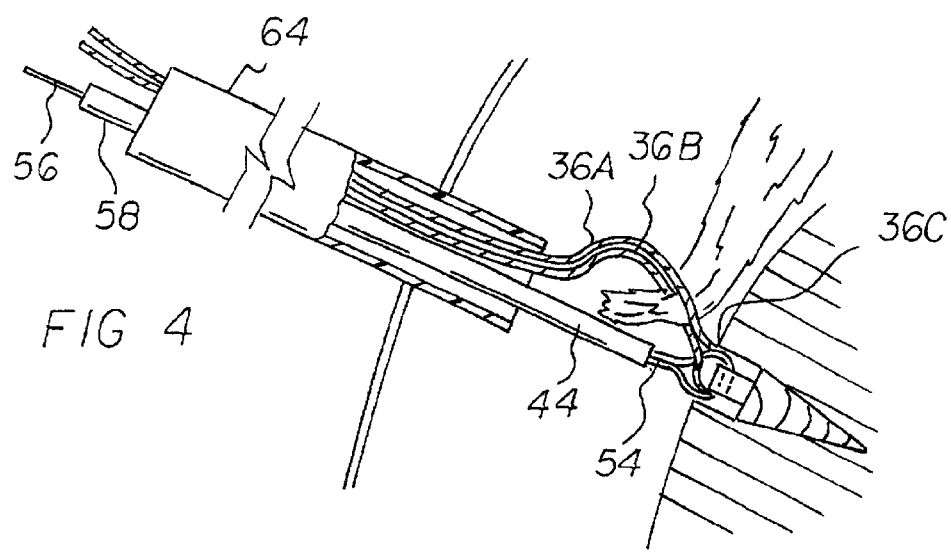
FIG. 4 is a cross sectional view similar to FIG. 2 but illustrating the first suture after positioning.
Figure 5:
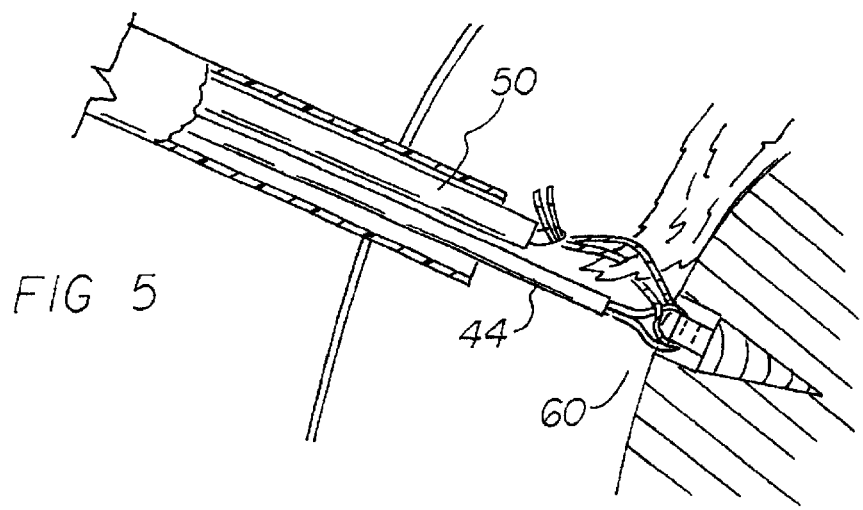
FIG. 5 is a cross sectional view similar to FIG. 2 and FIG. 4 but illustrating the first suture for being withdrawn by a lasso.
Figure 6:
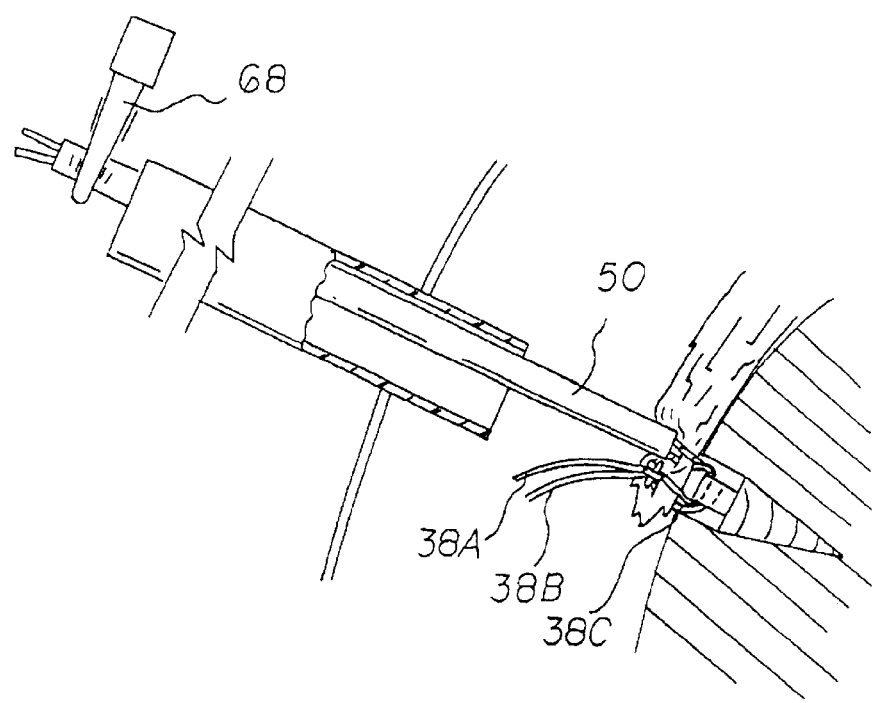
FIG. 6 is a cross sectional view similar to FIGS. 2, 4 and 5 but illustrating the second suture after the tying of the second knot with the first suture within the first supplemental sleeve.

With reference now to the drawings, and in particular to FIG. 1 thereof, the preferred embodiment of the new and improved suture management method and system embodying the principles and concepts of the present invention and generally designated by the reference numeral 10 will be described.

The present invention, the suture management method and system 10 is comprised of a plurality of components and steps. Such components in their broadest context include a tubular guide, a pair of sutures, and at least one hollow sleeve. Such components are individually configured and the components and steps are correlated with respect to each other so as to attain the desired objective.

The method and system is used by a surgeon while tying knots in sutures during surgery for a patient who has a bone 14 which would normally have a tendon attached to an exterior surface 16. A tendon 20 of the patient has an end 22 which was previously attached to the surface of the bone.

The method includes the step of providing a tubular guide 26. The guide has an anchoring screw 28. The screw has a threaded lower end 30. The screw also has an upper end 32 removably supported by the guide. An eyelet 34 is provided between the upper and lower ends.

The next step is providing a pair of sutures. The sutures include a first suture 36 of a first color and a second suture 38 of a second color. In the alternative, the sutures could be of the same color but different in visual characteristics. Each suture has two free ends 36A, 36B, 38A, 38B. Each suture also has a central portion 36C, 38C between its free ends. The central portion of both sutures is positioned through the eyelet of the screw.

The next step is providing a pair of primary sleeves. The primary sleeves include a first sleeve 42 and a second sleeve 44. Each primary sleeve is hollow. Each primary sleeve has an interior diameter to receive there through one suture. Each primary sleeve also has an exterior diameter less than half the interior diameter of the tubular guide. Each primary sleeve also has a length less than the distance between the free ends and the eyelet.

The next step is providing a pair of supplemental sleeves. The sleeves include a first supplemental sleeve 48 and a second supplemental sleeve 50. Each supplemental sleeve is hollow with an interior diameter to receive one suture there through. Each supplemental sleeve also has an exterior diameter. Each supplemental sleeve also has a length less than the distance between the free ends and the eyelet.

The next step is providing a clip to apply a holding force to one supplemental sleeve with a suture therein so as to preclude relative movement between the sleeve and the suture.

The next step is providing a slender plastic lasso 54. The lasso has a proximal end 56 constituting a handle 58. The lasso has a distal end formed as a resilient loop 60 adapted to maintain an opening when not under restraint by its positioning within a supplemental sleeve. The lasso has of a length greater than the supplemental sleeve.

The next step is introducing a cannula 64 into a patient. Next the tubular guide with the screw and the pair of sutures is introduced through the cannula into the patient. Then the screw and sutures are attached into the surface of the bone with the screw and central portions of the sutures beneath the surface of the bone. The ends of the sutures extend through the cannula to outside the patient with the suture of each color being individually constrained by a primary sleeve.

The next step is retracting the tubular guide from the screw and from the cannula.

The next step is contacting the tendon with the distal end of a supplemental sleeve to provide a temporary reduction for holding the tender to where it is intended to be positioned until a knot is formed for a final fixation.

The next step is removing the first primary sleeve from the first suture and from the cannula.

The next step is manipulating the first suture as by forming a stitch in the tendon.

The next step is positioning the first supplemental sleeve through the cannula. Then the lasso is extended through the first supplemental sleeve and the first suture is captured with the lasso. The lasso and the first suture are pulled exterior of the patient.

The next step is applying the slip to the first supplemental sleeve and first suture to create a holding force between the first supplemental sleeve and first suture and thereby preclude relative movement.

The next step is removing the second primary sleeve from the second suture and from the cannula.

The next step is manipulating the second suture as by forming a stitch in the tendon.

The next step is positioning the second supplemental sleeve through the cannula. Then the lasso is extended through the second supplemental sleeve. The second suture is then captured with the lasso. Next, the lasso and the second suture are pulled exterior of the patient.

The next step is removing a supplemental sleeve and manipulating a suture as may be needed.

The final step in the method is trimming the sutures and removing the trimmed ends of the sutures and the supplemental sleeves and lasso through the cannula and from the patient.

In addition to the above described method, the present invention includes a suture management system 10 for aiding a surgeon while tying knots in sutures during surgery in a manner to preclude suture tangling. First provided as part of the system is a tubular guide 26. The tubular guide has an anchoring screw 28. The anchoring screw has a threaded lower end 30 and an upper end 32 removably supported by the guide. An eyelet 34 is provided between the upper and lower ends.

A pair of sutures is next provided. The sutures include a first suture 36 of a first color and a second suture 38 of a second color. Each suture has two free ends 36A, 36B, 38A, 38B. Each suture also has a central portion 36C, 38C between its two free ends. The central portion of both sutures is positioned through the eyelet of the screw.

Next provided is a pair of primary sleeves. The primary sleeves include a first sleeve 42 and a second sleeve 44. Each sleeve is hollow with an interior diameter to receive there through one suture. Each sleeve has an exterior diameter less than half the interior diameter of the tubular guide. Each sleeve has a length less than the distance between the free ends and the eyelet.

A pair of supplemental sleeves is also provided. The supplemental sleeves include a first supplemental sleeve 48 and a second supplemental sleeve 50. Each supplemental sleeve is hollow with an interior diameter to receive one suture there through. Each supplemental sleeve has an exterior diameter. Each supplemental sleeve also has a length less than the distance between the free ends and the eyelet.

Finally, a slender plastic lasso 54 is provided. The lasso has a proximal end 56 constituting a handle 58. The lasso also has a distal end formed as a resilient loop 60 adapted to maintain an opening when not under restraint by its positioning within a supplemental sleeve. The lasso has a length greater than the supplemental sleeve.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is now desired to limit the invention to the exact construction and operation shown and described, and accordingly, all suitable modifications and equivalents may be resorted to, falling within the scope of the invention.

What is claimed as being new and desired to be protected by Letters Patent of the united states is as follows:

1. A suture management method for aiding a surgeon while tying knots in sutures during surgery in a manner to preclude suture tangling comprising, in combination, the steps of:

providing a bone of a patient having an exterior surface with a tendon normally attached thereto;

providing a tendon of a patient having an end previously attached to the surface of the bone;

providing a tubular guide with an anchoring screw having a threaded lower end and an upper end removably supported by the guide and with an eyelet between the upper and lower ends;

providing a pair of sutures including a first suture of a first color and a second suture of a second color, each suture having two free ends and a central portion there between, the central portion of both sutures positioned through the eyelet of the screw;

providing a pair of primary sleeves including a first sleeve and a second sleeve, each sleeve being hollow with an interior diameter to receive there through one suture and with an exterior diameter less than half the interior diameter of the tubular guide and a length less than the distance between the free ends and the eyelet;

providing a pair of supplemental sleeves including a first supplemental sleeve and a second supplemental sleeve, each supplemental sleeve being hollow with an interior diameter to receive one suture there through and an exterior diameter and a length less than the distance between the free ends and the eyelet;

providing a clip to apply a holding force to one supplemental sleeve with a suture therein so as to preclude relative movement there between;

providing a slender plastic lasso having a proximal end constituting a handle and a distal end formed as a resilient loop adapted to maintain an opening when not under restraint by its positioning within a supplemental sleeve, the lasso having of a length greater than the supplemental sleeve;

introducing a cannula into a patient and then introducing the tubular guide with the screw and the pair of sutures through the cannula into the patient and then attaching the screw and sutures into the surface of the bone with the screw and central portions of the sutures beneath the surface of the bone such that the ends of the sutures extend through the cannula to outside the patient with the suture of each color being individually constrained by a primary sleeve;

retracting the tubular guide from the screw and from the cannula;

contacting the tendon with the distal end of a supplemental sleeve to provide a temporary reduction for holding the tendon to where it is intended to be positioned until a knot is formed for a final fixation;

removing the first primary sleeve from the first suture and from the cannula;

manipulating the first suture as by forming a stitch in the tendon;

positioning the first supplemental sleeve through the cannula and then extending the lasso through the first supplemental sleeve and capturing the first suture with the lasso and then pulling the lasso and the first suture exterior of the patient;

applying the slip to the first supplemental sleeve and first suture to create a holding force there between and thereby preclude relative movement;

removing the second primary sleeve from the second suture and from the cannula;

manipulating the second suture as by forming a stitch in the tendon;

positioning the second supplemental sleeve through the cannula and then extending the lasso through the second supplemental sleeve and capturing the second suture with the lasso and then pulling the lasso and the second suture exterior of the patient;

removing a supplemental sleeve and manipulating a suture as may be needed; and trimming the sutures and removing the trimmed ends of the sutures and the supplemental sleeves and lasso through the cannula and from the patient.

2. A suture management system for aiding a surgeon while tying knots in sutures during surgery in a manner to preclude suture tangling comprising, in combination:

a tubular guide with an anchoring screw having a threaded lower end and an upper end removably supported by the guide and with an eyelet between the upper and lower ends;

a pair of sutures including a first suture of a first color and a second suture of a second color, each suture having two free ends and a central portion there between, the central portion of both sutures positioned through the eyelet of the screw;

a pair of primary sleeves including a first sleeve and a second sleeve, each sleeve being hollow with an interior diameter to receive there through one suture and with an exterior diameter less than half the interior diameter of the tubular guide and a length less than the distance between the free ends and the eyelet;

a pair of supplemental sleeves including a first supplemental sleeve and a second supplemental sleeve, each supplemental sleeve being hollow with an interior diameter to receive one suture there through and an exterior diameter and a length less than the distance between the free ends and the eyelet; and a slender plastic lasso having a proximal end constituting a handle and a distal end formed as a resilient loop adapted to maintain an opening when not under restraint by its positioning within a supplemental sleeve, the lasso having of a length greater than the supplemental sleeve.

3. The system as set forth in claim 2 and further including a clip to apply a holding force to one supplemental sleeve with a suture therein so as to preclude relative movement there between.

4. A suture management system comprising:

a tubular guide with an anchoring screw having a threaded lower end and an upper end removably supported by the guide and with an eyelet between the upper and lower ends;

a pair of sutures including a first suture of a first visual characteristic and a second suture of a second visual characteristic, each suture having two free ends and a central portion positioned through the eyelet; and at least one hollow sleeve receiving there through an associated suture wherein the sleeve includes a pair of primary sleeves including a first sleeve and a second sleeve, each sleeve being hollow with an interior diameter to receive there through one suture and with an exterior diameter less than half the interior diameter of the tubular guide and a length less than the distance between the free ends and the eyelet.

5. A suture management system comprising:

a tubular guide with an anchoring screw having a threaded lower end, and an upper end removably supported by the guide and with an eyelet between the upper and lower ends;

a pair of sutures including a first suture of a first visual characteristic and a second suture of a second visual characteristic, each suture having two free ends and a central portion positioned through the eyelet; and at least one hollow sleeve receiving there through an associated suture wherein the sleeve includes a pair of supplemental sleeves including a first supplemental sleeve and a second supplemental sleeve, each supplemental sleeve being hollow with an interior diameter to receive one suture there through and an exterior diameter and a length less than the distance between the free ends and the eyelet.

6. A suture management system comprising:

a tubular guide with an anchoring screw having a threaded lower end and an upper end removably supported by the guide and with an eyelet between the upper and lower ends;

a pair of sutures including a first suture of a first visual characteristic and a second suture of a second visual characteristic, each suture having two free ends and a central portion positioned through the eyelet; and at least one hollow sleeve receiving there through an associated suture wherein the sleeve includes a slender plastic lasso having a proximal end constituting a handle and a distal end formed as a resilient loop adapted to maintain an opening when not under restraint by its positioning within a sleeve, the lasso having of a length greater than the sleeve.

7. A suture management system comprising:

a tubular guide with an anchoring screw having a threaded lower end and an upper end removably supported by the guide and with an eyelet between the upper and lower ends;

a pair of sutures including a first suture of a first visual characteristic and a second suture of a second visual characteristic, each suture having two free ends and a central portion positioned through the eyelet; and at least one hollow sleeve receiving there through an associated suture wherein the sleeve includes a pair of primary sleeves including a first sleeve and a second sleeve, each sleeve being hollow with an interior diameter to receive there through one suture and with an exterior diameter less than half the interior diameter of the tubular guide and a length less than the distance between the free ends and the eyelet and a pair of supplemental sleeves including a first supplemental sleeve and a second supplemental sleeve, each supplemental sleeve being hollow with an interior diameter to receive one suture there through and an exterior diameter and a length less than the distance between the free ends and the eyelet.

* * * * *